United States Patent [19]

Hasse

[11] Patent Number: 4,657,539
[45] Date of Patent: Apr. 14, 1987

[54] WASTE CONTAINMENT GARMENT HAVING ELASTICIZED BARRIER WALL LEG FLAPS

[75] Inventor: Margaret H. Hasse, Wyoming, Ohio

[73] Assignee: The Procter & Gamble Company, Cincinnati, Ohio

[21] Appl. No.: 727,490

[22] Filed: Apr. 26, 1985

[51] Int. Cl.$^4$ .............................................. A61F 13/16
[52] U.S. Cl. .................................................. 604/385 A
[58] Field of Search ............... 604/385 R, 385 A, 396, 604/393, 386, 394, 395

[56] References Cited

U.S. PATENT DOCUMENTS 3,572,342  3/1971  Lindquist et al. .
3,860,003  1/1975  Buell .
4,040,423  8/1977  Jones, Sr. .
4,041,950  8/1977  Jones, Sr. .

FOREIGN PATENT DOCUMENTS 866527  10/1978  Belgium .

Primary Examiner—John D. Yasko
Attorney, Agent, or Firm—Donald E. Hasse; Fredrick H. Braun; Richard C. Witte

[57] ABSTRACT

A waste containment garment such as a disposable diaper or a disposable adult brief having elasticized leg flaps which are configured and disposed to present longitudinally extending, inboard facing barrier walls that are positioned outboard from the side edges of the crotch portion of the absorbent core. Such barrier walls function as dams against lateral flow of body wastes, particularly of a runny solids nature.

14 Claims, 6 Drawing Figures

WASTE CONTAINMENT GARMENT HAVING ELASTICIZED BARRIER WALL LEG FLAPS

TECHNICAL FIELD

The present invention relates to disposable waste containment garments, such as disposable diapers and adult incontinent briefs, having elasticized leg flaps that contain longitudinally extending, inboard facing barrier walls which function as dams against lateral flow of body wastes. More particularly, the invention pertains to such garments having resilient leg cuff members in the elasticized leg flaps to increase the garment's waste containment characteristics and wearing comfort.

BACKGROUND OF THE INVENTION

In the field of disposable waste containment garments, there is a continuing effort to improve both wearing comfort and the ability to contain body wastes. Elasticized disposable diapers providing superior fit and liquid waste containment are disclosed in U.S. Pat. No. 3,860,003, issued to Buell on Jan. 14, 1975. The present invention is directed to improving containment of such garments having elasticized leg flaps, particularly containment of runny solids waste material.

Contemporary disposable diaper topsheets have small pores which can prevent the diaper core from efficiently absorbing or capturing runny waste material. In such cases, the waste material tends to "float" on the topsheet's surface. Over a short period of time, particularly if the wearer is active, the runny waste material can become smeared on the wearer's skin surfaces and work its way past the elastic leg flaps. The present invention improves containment of such runny waste material by providing elasticized leg flaps with barrier walls that dam lateral flow of body wastes and minimize smearing on skin surfaces. In addition, the padded (i.e., resilient) elastic leg flaps in accordance with the present invention increase wearing comfort.

U.S. Pat. No. 3,572,342, issued to Lindquist et al. on Mar. 23, 1971, describes an attempt to improve a disposable diaper's waste containment characteristics by securing strips of resilient hydrophobic polymer foam along each side of a diaper's upper surface to provide a seal between the diaper's outer portion and the wearer's legs. However, since the diaper is not provided with means for pressing the sealing strips against the wearer's legs, it is inadequate for containing runny waste material.

In light of the above, a principle object of the present invention is to provide a disposable waste containment garment having elasticized leg flaps that include longitudinally extending inboard facing barrier walls which function as dams against lateral flow of body wastes.

Another object of the present invention is to improve the wearing comfort of an elasticized disposable waste containment garment by padding the elastics with a resilient leg cuff member that provides a snug fit around the legs without causing discomfort to the wearer.

SUMMARY OF THE INVENTION

In accordance with the present invention, a waste containment garment having an absorbent core, a backsheet, and elastically contractible, longitudinally extending leg flaps is provided with means for presenting longitudinally extending, inboard facing barrier walls in the leg flaps to dam lateral flow of the user's body wastes. In a particularly preferred embodiment, the means for presenting the barrier walls comprise longitudinally extending leg cuff members disposed superjacent the user's side of the elastic in the leg flaps, which leg cuff members are sufficiently resilient with respect to the elastic to be longitudinally contracted thereby so that the leg flaps maintain sealing engagement with skin surfaces of the wearer during use while providing a comfortable fit.

BRIEF DESCRIPTIONS OF THE DRAWINGS

While the specification concludes with claims which particularly point out and distinctly claim the subject matter regarded as forming the present invention, it is believed the invention will be better understood from the following description taken in conjunction with the accompanying drawings in which like designations are used to designate substantially identical elements, and in which:

DETAILED DESCRIPTION OF THE INVENTION

Figure 1:
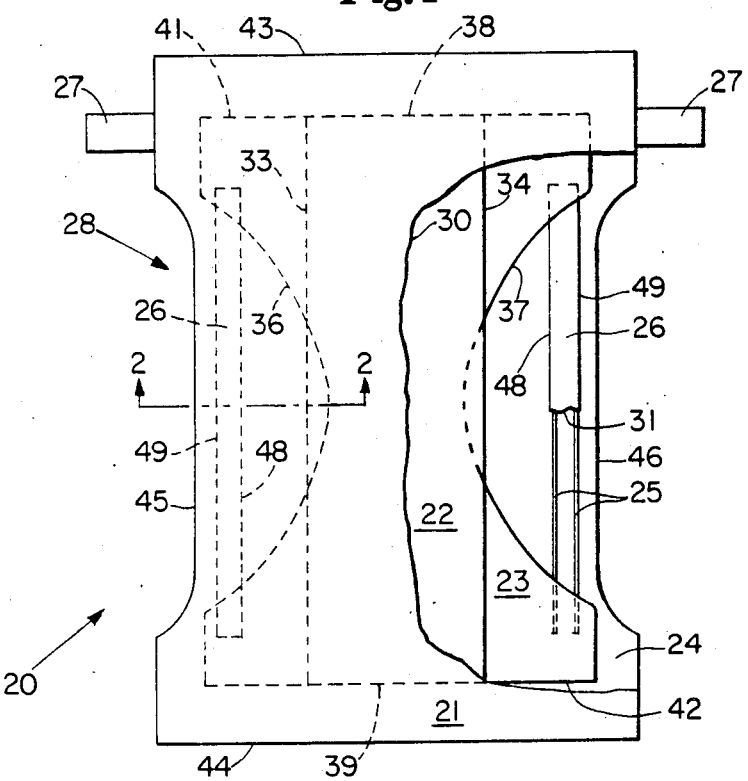
FIG. 1 is a plan view of an exemplary disposable diaper embodiment of the invention having portions torn away to reveal underlying structure.

An exemplary disposable waste containiment garment embodiment of the present invention is shown in its flat-out state (i.e., with all elastic induced contraction pulled out) in FIG. 1 as disposable diaper 20 which comprises a topsheet 21, a top tissue 22, an absorbent core 23, a backsheet 24, elastic means which are shown as strands 25 of elastic, leg cuff members 26, and tape-tab fasteners 27. This construction comprises longitudinally elasticized leg flaps 28 which comprise portions of the topsheet 21, the backsheet 24, the strands 25 of elastic, and the leg cuff members 26. As also shown in FIG. 1: a portion of topsheet 21 is torn away along line 30; a portion of one leg cuff member 26 is torn away along line 31; the longitudinal side edges of top tissue 22 are designated 33 and 34; the side edges of absorbent core 23 are designated 36 and 37; the end edges of top tissue 22 are designated 38 and 39 and are coextensive with the end edges of absorbent core 23 which are designated 41 and 42; the topsheet 21 and the backsheet 24 are coextensive and have common end edges 43 and 44 and common side edges 45 and 46; and each leg cuff member 26 has longitudinally extending edges which are designated inboard edge 48 and outboard edge 49.

Figure 2:
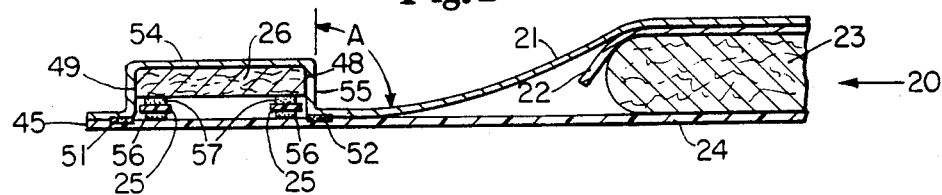
FIG. 2 is an enlarged scale, fragmentary sectional view taken along section line 2—2 of FIG. 1, and wherein thicknesses of some of the elements are exaggerated to more clearly depict their presence and relationships.

Referring now to FIG. 2 which is a fragmentary, enlarged scale sectional view of diaper 20, FIG. 1, the topsheet 21 is shown to be U-folded to form a channel over leg cuff member 26 and secured to backsheet 24 with longitudinally extending glue beads 51 and 52 which are disposed immediately adjacent outboard edge 49 and inboard edge 48, respectively. As thus formed and secured, the top surface of the U-folded portion of the topsheet is designated 54, and the inboard vertically extending portion of the U-folded topsheet is designated barrier wall 55. Angle A represents the angle between barrier wall 55 and topsheet 21, and is preferably equal to about 90°, although it can extend up to about 135°. As further shown in FIG. 2, the elastic strands 25 are disposed under the longitudinally extending edges of leg cuff member 26 and are secured to backsheet 24 with glue beads 56 and to leg cuff member 26 with glue beads 57. Additional glue beads or sprayed adhesive (not shown) are provided to secure the topsheet/top-tissue/core/backsheet together to provide structural integrity for diaper 20.

Briefly, referring to FIGS. 1 and 2, the leg flaps 28 of diaper 20 are elastically contractible by virtue of the physical properties of their materials of construction and the presence of elastic strands 25. Strands 25 are sufficiently tensioned to cause the top surface 54 of the topsheet cover over leg cuff member 26 to contact skin areas of the user. Thus positioned and tensioned, the vertically extending barrier wall 55 acts as a dam to lateral flow of body wastes, particularly of a runny nature. As will be described more fully below, alternate embodiments of the invention are provided which comprise uncovered leg cuff members in which the inboard edge/surface 48 of each leg cuff member functions as such a dam to lateral waste flow. Additionally, another alternate embodiment comprises leg cuff members which are covered by return folded edge portions of the backsheet. In the latter embodiment, the portion of the backsheet which extends vertically and covers the inboard edge of the leg cuff member acts as such a dam to lateral waste flow. Accordingly, all of these vertical wall configurations are hereby generically designated dam means for substantially damming up (i.e., blocking) lateral flow of body wastes.

Topsheet 21 can be any compliant, soft feeling, non-irritating (to the wearer's skin), liquid permeable, planar material. It can be constructed of porous paper made from natural or synthetic fibers or mixtures thereof, nonwoven fabric made from natural or synthetic fibers or mixtures thereof, apertured plastic film, porous foam, or the like. Preferably, it is made of a hydrophobic material to isolate the wearer's skin from fluids in the absorbent core. Examples of suitable topsheets are described in U.S. Pat. No. 3,860,003, Buell, issued Jan. 14, 1975, incorporated herein by reference.

A suitable topsheet is spun-bonded nonwoven polyester fabric made from fibers of from about 2.2 to about 2.5 denier, having a basis weight of about 17 grams per square meter. Another preferred topsheet material comprises about 65% staple length, 1.5 denier polyester fibers (such as Kodel type 411 polyester fibers as sold by Tennessee Eastman Corporation, Kingsport, Tenn.); about 15% crimped, staple length, 1.5 denier rayon fibers; and about 20% acrylic copolymer binder (such as Celanese CPE 8335, as sold by Celanese Corporation of Charlotte, N.C.). "Staple length" refers to fibers having a length of at least 15 mm.

Suitable topsheets can also be constructed from aperatured plastic films such as those described by Radel and Thompson in U.S. Pat. No. 4,342,314, issued Aug. 3, 1982 and incorporated herein by reference. Another aperatured thermoplastic film useful as a topsheet is described in U.S. Pat. No. 4,341,217 issued to Ferguson and Landgrigan on July 27, 1982, which patent is also incorporated herein by reference. Suitable topsheet can be formed from a liquid impermeable material provided with tapered capillaries as described in U.S. Pat. No. 3,929,135, issued to Thompson on Dec. 30, 1975, incorporated herein by reference.

A preferred topsheet is constructed from polypropylene fibers which have been carded and thermally bonded in a spaced-apart pattern. Fibers about 3.8 cm long and of from about 1.5 to about 3.0 denier are suitable. A preferred sheet has a basis weight of about 22 grams per square meter.

Although disposable diapers commonly and preferably have topsheets, they can be constructed without a topsheet (as, for example, when the surface of the absorbent element serves the function of a topsheet). The present invention will function in such a diaper, and its use therein is contemplated.

Top tissue 22 can be made from any permeable material known to those skilled in the art. Preferably, the material possesses wet strength characteristics. Particularly satisfactory results are obtained when top tissue 22 is constructed from sheets of wet strength tissue paper having a basis weight of about 16 grams per square meter and having an air permeability of about 30.5 cubic meters per minute square meter ($M^2$) of tissue at a pressure differential of about 12.7 millimeters of water.

Top tissue 22 is an optional, but preferred, element in the disposable waste containment garments herein. A corresponding back tissue placed between the absorbent core 23 and backsheet 24 can also optionally be included but is not shown in the figures.

Absorbent core 23 can be made of any material which is generally compressible, conformable, non-irritating to the wearer's skin, capable of absorbing and retaining fluids, and capable of containing solid waste material.

In the embodiment illustrated in FIG. 1, absorbent core 23 has an hourglass shape, but rectangular shapes and others can also be used. The lateral and longitudinal dimensions of absorbent core 23 are selected depending on the size of the infant wearing the disposable diaper. When disposable diaper 20 is selected for wear by an infant weighing from about 5 to about 11 kilograms, absorbent core 23 is about 12.5 in. (31.8 cm) wide (lateral dimension) and about 17.8 in. (45.1 cm) long (longitudinal dimension). Other sizes for larger or smaller infants can be readily selected by those skilled in the art.

Absorbent core 23 can be constructed from any of a variety of materials commonly used in disposable absorbent articles, such as those described in the above mentioned Buell patent. Examples of suitable absorbent materials include creped cellulose wadding, absorbent foams, absorbent sponges, super absorbent polymers, and, preferably, comminuted and airlaid wood pulp commonly referred to as absorbent fluff. In an embodiment of the size hereinbefore mentioned, when absorbent core 23 comprises absorbent fluff, it weighs from about 30 to about 56 grams and has an absorbent capacity of from about 4 to about 12 grams of water per gram of absorbent fluff. It has a density of from about 0.1 to about 0.2 grams per cubic centimeter.

Backsheet 24 can be made of any compliant, non-irritating, generally planar material which is impermeable to fluid body discharges. Suitable materials are described in the above incorporated patent to Buell. A particularly preferred backsheet is formed from polyethylene film having a thickness of from about 1 mil (0.025 mm) to about 1.5 mils (0.038 cm).

Breathable backsheets useful in the present invention are described in U.S. Pat. No. 3,156,242, issued to Crowe, Jr. on Nov. 10, 1964; U.S. Pat. No. 3,881,489, issued to Hartwell on May 6, 1975; U.S. Pat. No. 3,989,867, issued to Sisson on Nov. 2, 1976; and U.S.

Pat. No. 4,341,216, issued to Obenour on July 27, 1982; all incorporated herein by reference.

The size of backsheet 24 is dictated by the size of absorbent core 23 and the exact diaper design selected.

Elastic means shown in FIG. 1 as strands 25 of elastic are secured to leg flaps 28 in an elastically contractible condition so that in a normally unrestrained configuration, elastic strands 25 effectively contract or gather the leg flaps 28. Elastic strands 25 can be secured to leg flaps 28 in an elastically contractible condition in at least two ways. For example, elastic strands 25 may be stretched and secured to leg flaps 28 while the leg flaps are in an uncontracted condition. Alternatively, leg flaps 28 can be contracted, for example by pleating, and elastic strands 25 secured to the contracted leg flaps 28 while elastic strands 25 are in their relaxed or unstretched condition.

Preferably, elastic strands 25 develop a skin contact pressure in use of from about 0.007 to about 0.17 kilogram per square centimeter. To provide the proper skin contact pressure, elastic strands 25 will preferably have a contractual force in its stretched condition of from about 10 to about 200 grams. Elastic strands should provide such a contractional force and thus establish its stretched condition at an elongation from its relaxed state of from about 50% to about 400%. One elastic element which has been found to be suitable is an elastic tape having a cross section of 0.18 millimeter by 1.5 millimeter and made from natural rubber as available from East Hampton Rubber Company of Stuart, Va., under the trademark L-1900 Rubber Compound. Other suitable elastic elements can be made from natural rubber elastic tapes sold under the trademark Fulflex 9211 by Fulflex Company of Scotland, N.C. The length of elastic element 31 in general is dictated by diaper design. In the embodiment illustrated in FIG. 1, elastic element extends essentially the entire length of leg flaps 28.

In diaper 20 FIG. 2, elastic strands 25 are secured to the backsheet 24 with glue beads 56 and to leg cuff member 26 with glue beads 57. Glue beads herein are preferably hot melt adhesives such as marketed by Findley Adhesives Incorporated, Elmgrove, Wis. as Findley Adhesives 581. A more detailed description of the manner in which elastic strands 25 should be positioned and secured to disposable diapers and briefs can be found in the above incorporated patent to Buell and in U.S. Pat. No. 4,253,461, issued to Strickland and Visscher on Mar. 3, 1981, incorporated herein by reference. It should also be noted that one or more elastic strands 25 can be used to elasticize each leg flap 28.

Leg cuff member 26 can be made of any material that is sufficiently resilient with respect to the elastic means to be longitudinally contractible thereby so that the leg flaps maintain sealing engagement with skin surfaces of the wearer during use. Examples of such resilient material are polypropylene, polyester, rayon, nylon, and polyurethane foam. Preferably, leg cuff member 26 is made of a resilient material that recovers at least about 50%, more preferably at least about 70%, of its initial thickness at 5 minutes after being subjected to a pressure of 0.5 pounds per square inch (35.2 grams per square centimeter) for 5 minutes. The resilient material is preferably a substantially hydrophobic material having a basis weight of from about 30 to about 150, preferably from about 50 to about 100, grams per square meter. More preferably, it is a nonwoven web of thermoplastic material comprising polypropolene or polyester, particularly when such a web consists of interbonded thermoplastic filaments having a denier of from about 6 to about 15.

Each leg cuff member 26 has thickness or caliper of at least about 1 mm, and preferably from about 2 mm to about 10 mm, so that barrier wall 55 has a height of at least about 1 mm, preferably from about 2 mm to about 10 mm, as measured when diaper 20 is in its flat-out state with no load on leg cuff member 26. The leg cuff member 26 generally has a width of from about 5 mm to about 40 mm, preferably from about 10 mm to about 30 mm, and width to thickness ratio of from about 0.75 to about 8.0, preferably from about 1.0 to about 6.0. The leg cuff member 26 can have varying shapes provided it presents a longitudinally extending, inboard facing barrier wall effective for damming lateral flow of body wastes when included in leg flaps 28. For example, leg cuff member 26 can have a circular, square, trapezoidal or rectangular cross-sectional area. Rectangular cross-sectional areas are preferred because they provide a vertical inboard facing barrier wall 55.

Fastening tapes 27 are typically applied to the back waist corner portions of a disposable diaper to provide a fastening means to hold the diaper on an infant. Fastening tapes 27 can be any of those well known to those of ordinary skill in the art, such as the fastening tape disclosed in U.S. Pat. No. 3,646,937 issued to Gellert on Mar. 7, 1972. These fastening tapes, or other diaper fastening means, such as pins, are typically applied near the top edge of a diaper in its "in-use" configuration.

An exemplary disposable waste containment garment 20 of FIG. 1 was constructed in which the backsheet 24 was a matte-finish polyethylene film having a nominal thickness of about 1.2 mil (about 0.03 mm), and overall length and width of about 17.8 inches (45.1 cm) by about 12.5 inches (31.8 cm); the topsheet 21 was a nonwoven polypropylene web having a nominal thickness of about 3 to 5 mils (about 0.056 to 0.127 mm), and length and width about equal to the corresponding dimensions of the backsheet; the absorbent core 23 was an air laid batt of comminuted wood pulp fibers having a nominal weight of about 52 grams, a nominal caliper of about 7.1 mm, and length of about 15 inches (38.1 cm) and width of about 4 inches (10.2 cm) at the crotch; the strands 25 of elastic had a nominal unstretched thickness and width of about 0.2 and 2.4 mm, respectively, and had been stretched about one-hundred-twenty-five (125%) prior to being adhesively secured to the backsheet; the leg cuff members 26 were made of interbonded thermoplastic polypropylene fibers having a denier about 12 and a basis weight of about 65 grams per square yard (77.7 grams per square meter) and had a length of 9 in. (22.9 cm), a width of about 1 in. (2.5 cm) and a thickness of about 0.25 in. (0.6 cm), and were adhesively secured to the strands 25 of elastic in their stretched position; and the topsheet was adhesively secured to the backsheet whereby the longitudinal side edges of the garment (i.e., the elasticized leg flaps 28) had nominal extensions (i.e., their available stretch as a percent of their elastically contracted length) of about 36 percent or greater.

As further shown in FIG. 1, the elastic strands 25 extended longitudinally and were disposed adjacent the longitudinal side edges 36 and 37 of the absorbent core. The inboard edge of the elastic strand 25 disposed closest to the absorbent core 23 was spaced about 1.9 inches (about 4.8 cm) from the crotch region of the absorbent core. The inboard elastic strand 25 was spaced about 0.75 inches (1.9 cm) from the outboard elastic strand 25. As thus formed, the elasticized leg flaps 28 could be contracted and stretched without having to induce crumpling or longitudinal compression of the core, and stretching induced tension was available for sealingly engaging the leg flaps 28 with skin areas of a wearer. The leg cuff member 26 also maintained the desired spacing between the inboard and outboard elastic strands 25.

ALTERNATE EMBODIMENTS

For convenience of description, the alternate embodiments of the present invention shown in FIGS. 3 through 6 are described below only where they differ from the preferred embodiment shown in FIGS. 1 and 2.

Figure 3:
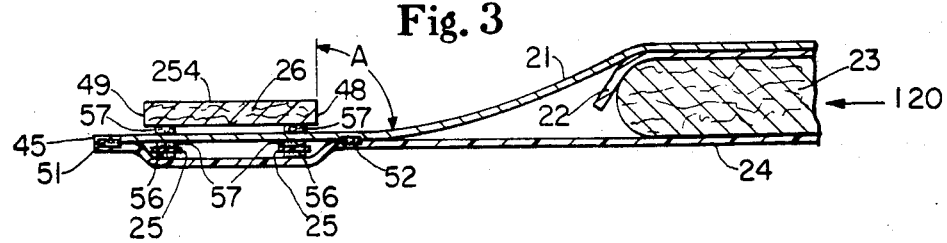
FIGS. 3 through 6 are sectional views similar to FIG. 2 except they are of alternate embodiments of the invention.

FIG. 3, alternate diaper 120, comprises a leg cuff member 26 that is placed over and secured to topsheet 21. The top surface of the uncovered leg cuff member 26 is designated 254. The vertical inboard edge 48 of leg cuff member 26 functions as the barrier wall described hereinbefore for damming lateral flow of body wastes.

Figure 4:
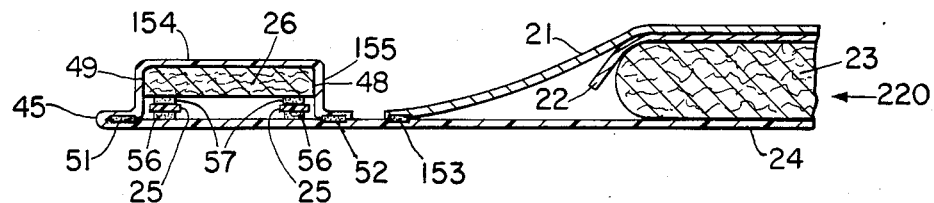

Referring now to alternate diaper embodiment 220, FIG. 4, topsheet 21 is terminated inboard of leg cuff member 26, and is secured to backsheet 24 with longitudinally extending glue bead 153. Backsheet 24 is return folded in a U-shape over leg cuff member 26 and secured to backsheet 24 with longitudinally extending glue beads 51 and 52 adjacent the inboard and outboard edges of leg cuff member 26. The top surface of the U-folded portion of the backsheet is designated 154 and the inboard vertically extending portion of the U-folded backsheet is designated barrier wall 155.

Figure 5:
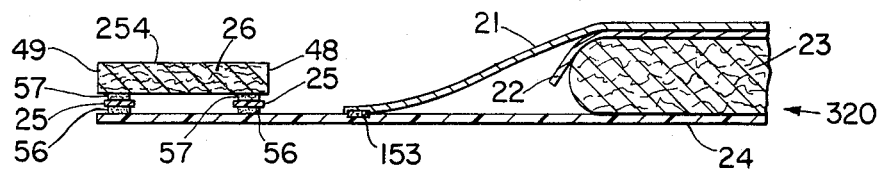

FIG. 5 shows a diaper embodiment 320 that is similar to diaper 220, FIG. 4, except that backsheet 24 terminates at the outboard edge 49 of leg cuff member 26 instead of being U-folded over it. The top surface of uncovered leg cuff member 26 is designated 254, and the vertical inboard edge 48 of leg cuff member 26 functions as the barrier wall for damming lateral flow of body waste.

Figure 6:
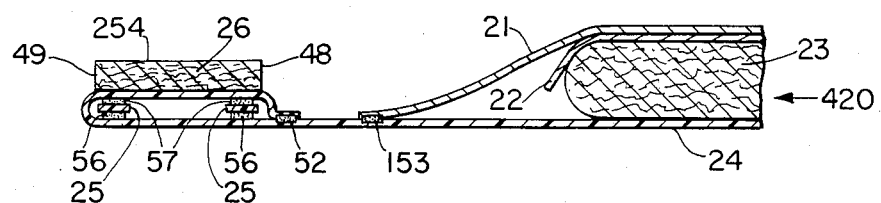

Diaper 420, FIG. 6, is similar to diaper 320, FIG. 5, except that backsheet 24 is return folded over strands 25 of elastic and secured to backsheet 24 with longitudinally extending glue bead 52. In this embodiment, inboard edge 48 of uncovered leg cuff member 26 presents a substantially vertical longitudinally extending barrier wall for damming lateral flow of body waste.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of this invention.

What is claimed is:

1. A disposable waste containment garment comprising:
   a liquid permeable topsheet;
   an absorbent core, said absorbent core having side edges;
   a liquid impermeable backsheet;
   said topsheet being secured to said backsheet, and said absorbent core being positioned between said topsheet and said backsheet;
   elastically contractible and longitudinally extending leg flaps, said leg flaps comprising those portions of said backsheet which extend outwardly beyond said side edges of said absorbent core;
   an elastic means for rendering said leg flaps longitudinally elastically contractible; and
   a leg cuff member affixed to each of said leg flaps, each of said leg cuff members having an inboard facing barrier wall at least ¾ inches from said side edges of said absorbent core,
   said barrier wall having a height of at least about 1 mm.

2. The disposable waste containment garment of claim 1, wherein said leg cuff members are sufficiently resilient with respect to the elasticity of said elastic means to be longitudinally contractible thereby so that inwardly facing surface areas of said leg flaps maintain sealing engagement with skin surfaces of the user during use.

3. In an improved disposable waste containment garment of the type comprising a topsheet, an absorbent core, a backsheet, and elastically contractible and longitudinally extending leg flaps, said leg flaps comprising portions of said backsheet disposed outboard from the side edges of said absorbent core in at least the crotch region of the core, and elastic means for rendering said leg flaps longitudinally elastically contractible, the improvement wherein each of said leg flaps further comprises means for presenting a longitudinally extending, inboard facing barrier wall for damming lateral flow of body wastes, said barrier wall having a height of at least about one millimeter; said means for presenting a longitudinally extending inboard facing barrier wall for damming lateral flow of the user's body wastes comprising a longitudinally extending leg cuff member that is disposed superjacent the user's side of said elastic means, said leg cuff member being sufficiently resilient with respect to the elasticity of said elastic means to be longitudinally contractible thereby so that inwardly facing surface areas of said leg flaps maintain sealing engagement with skin surfaces of said user during use; each of said leg flaps further comprising a side edge portion of said topsheet, and wherein each of said leg cuff members is disposed intermediate said elastic means and a said edge portion of said topsheet, and said edge portion of said topsheet is U-channel shaped over said leg cuff member and secured to a substantially planar portion of said backsheet adjacent both the inboard and outboard longitudinally extending edges of said leg cuff member.

4. The improved disposable waste containment garment of claim 3 wherein said topsheet is secured to said substantially planar portion of said backsheet immediately adjacent both the inboard and outboard longitudinally extending edges of said leg cuff member.

5. The improved disposable waste containment garment of claim 4 wherein said elastic means of each said leg flap comprises longitudinally extending elastic material disposed immediately subjacent the longitudinally extending inboard edge of its respective leg cuff member.

6. The improved disposable waste containment garment of claim 3 wherein each said leg cuff member has a thickness of from about 2 mm to about 10 mm.

7. The improved disposable waste containment garment of claim 3 wherein each said leg cuff member has a width of from about 10 mm to about 30 mm.

8. The improved disposable waste containment garment of claim 3 wherein each said leg cuff member has a width to thickness ratio from about 1.0 to about 6.0.

9. The improved disposable waste containment garment of claim 3 wherein each said leg cuff member has a substantially rectangular cross-sectional area.

10. The improved disposable waste containment garment of claims 3 or 5 wherein said leg cuff members are made of a substantially hydrophobic material having a basis weight of from about 30 to about 150 grams per square meter.

11. The improved disposable waste containment garment of claim 10 wherein said hydrophobic material is a nonwoven web of thermoplastic material comprising polypropylene or polyester.

12. The improved disposable waste containment garment of claim 11 wherein said nonwoven web consists of interbonded thermoplastic filaments having a denier of from about 6 to about 15.

13. The improved disposable waste containment garment of claim 12 wherein each said leg cuff member has a width to thickness ratio of from about 1.0 to about 6.0.

14. The improved disposable waste containment garment of claim 13 wherein each said leg cuff member has a width of from about 10 mm to about 30 mm, a thickness of from about 2 mm to about 10 mm, and a substantially rectangular cross-sectional area.

* * * * *